United States Patent
Conboy et al.

(10) Patent No.: US 10,265,372 B2
(45) Date of Patent: Apr. 23, 2019

(54) MOLECULAR COMPOSITION FOR ENHANCING AND REJUVENATING MAINTENANCE AND REPAIR OF MAMMALIAN TISSUES

(71) Applicant: The Regents of the University of California, Oakland, CA (US)

(72) Inventors: Irina M. Conboy, El Sobrante, CA (US); David Vernon Schaffer, Danville, CA (US); Hanadie Yousef, San Mateo, CA (US); Michael J. Conboy, El Sobrante, CA (US); Wendy Cousin, Berkeley, CA (US); Christian Elabd, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/327,309

(22) PCT Filed: Aug. 12, 2015

(86) PCT No.: PCT/US2015/044900
§ 371 (c)(1),
(2) Date: Jan. 18, 2017

(87) PCT Pub. No.: WO2016/025629
PCT Pub. Date: Feb. 18, 2016

(65) Prior Publication Data
US 2017/0239320 A1 Aug. 24, 2017

Related U.S. Application Data

(60) Provisional application No. 62/036,473, filed on Aug. 12, 2014.

(51) Int. Cl.
| | | |
|---|---|---|
| *A61K 38/11* | (2006.01) | |
| *A61K 38/18* | (2006.01) | |
| *A61K 31/444* | (2006.01) | |
| *A61K 31/536* | (2006.01) | |
| *C12N 5/077* | (2010.01) | |
| *C12N 5/0797* | (2010.01) | |
| *G01N 33/50* | (2006.01) | |

(52) U.S. Cl.
CPC ............ *A61K 38/11* (2013.01); *A61K 31/444* (2013.01); *A61K 31/536* (2013.01); *A61K 38/1841* (2013.01); *C12N 5/0623* (2013.01); *C12N 5/0658* (2013.01); *G01N 33/502* (2013.01); *C12N 2501/30* (2013.01); *C12N 2501/727* (2013.01); *C12N 2501/999* (2013.01)

(58) Field of Classification Search
CPC .. A61K 38/11; A61K 38/1841; A61K 31/444; A61K 31/536
See application file for complete search history.

(56) References Cited

U.S. PATENT DOCUMENTS

| | | | |
|---|---|---|---|
| 5,795,715 A | 8/1998 | Livache et al. | |
| 6,333,313 B1 | 12/2001 | Copland et al. | |
| 8,748,564 B2 | 6/2014 | Wisniewski et al. | |
| 2004/0235956 A1* | 11/2004 | Quay .................. | A61K 31/395 514/573 |
| 2004/0266842 A1 | 12/2004 | Gaster et al. | |
| 2005/0208027 A1 | 9/2005 | Conboy et al. | |
| 2005/0245520 A1 | 11/2005 | Dodic et al. | |
| 2006/0194845 A1 | 8/2006 | Sawutz | |
| 2007/0117794 A1 | 5/2007 | Rahman et al. | |
| 2012/0225875 A1* | 9/2012 | Jonczyk .............. | C07D 401/12 514/235.2 |
| 2013/0085106 A1 | 4/2013 | Pedersen et al. | |
| 2013/0196437 A1 | 8/2013 | Stankewicz et al. | |

FOREIGN PATENT DOCUMENTS

| | | |
|---|---|---|
| WO | 9506764 | 3/1995 |
| WO | 9523225 | 8/1995 |
| WO | 0168836 | 9/2001 |
| WO | 03010180 | 2/2003 |

OTHER PUBLICATIONS

Bashkin et al. (1995) "Ribozyme mimics as catalytic antisense reagents" Appl. Biochem. Biotechnol. 54(1-3):43-56.
Beigelman et al. (1995) "Synthesis of 2'-modified nucleotides and their incorporation into hammerhead ribozymes" Nucl. Acids Res. 23(21):4434-4442.
Bhattacharyya et al. (1990) "RNA bulges and the helical periodicity of double-stranded RNA" Nature 343:484.
Elabd et al. (2014) "Oxytocin is an age-specific circulating hormone that is necessary for muscle maintenance and regeneration" Nature Communications 5:4082.
Fire et al. (1998) "Potent and specific genetic interference by double-stranded RNA in Caenorhabditis elegans" Nature 391:806-811.
Inman (2011) "Switching TGFβ from a tumor suppressor to a tumor promoter" Current opinion in genetics & development 21:93-99.
Langer (1990) "New Methods of Drug Delivery" Science 249:1527-1533.

(Continued)

*Primary Examiner* — Daniel C Gamett
(74) *Attorney, Agent, or Firm* — Edward J. Baba; Bozicevic, Field & Francis LLP (57) ABSTRACT

Methods, pharmaceutical compositions, and kits are provided for treating a subject with an effective amount of an oxytocin receptor (OXTR) agonist and an effective amount of an ALK5 antagonist. In certain aspects, the OXTR agonist may be oxytocin or an oxytocin analog (e.g., a small molecule). The ALK 5 antagonist may be a small molecule, such as 2-(3-(6-Methyl-pyridin-2-yl)-1H-pyrazol-4-yl)-1,5-naphthyridine, LY2157299, A 83-01, D 4476, GW 788388, LY 364947, Rep Sox, SB 431542, SB 505124, SB 525334, or SD 208. In certain aspects, the amounts of the OXTR agonist and ALK5 antagonist may be sufficient to induce muscle regeneration and/or neural cell regeneration in the subject.

38 Claims, 4 Drawing Sheets

(56) References Cited

OTHER PUBLICATIONS

Reagan-Shaw et al. (2007) "Dose translation from animal to human studies revisited" The FASEB Journal 22:659-661.
Sadhu et al. (1987) "In vitro synthesis of double stranded RNA and measurement of thermal stability: effect of base composition, formamide and ionic strength" Biochem. Int. 14:1015.
Sharp (1999) "RNAi and double-strand RNA" Genes and Development 13:139-141.
Wianny et al. (1998) "Mouse polo-like kinase 1 associates with the acentriolar spindle poles, meiotic chromosomes and spindle midzone during oocyte maturation" Chromosoma 107:430-439.
Zernicka-Goetz et al. (1997) "Following cell fate in the living mouse embryo" Development 124:1133-1137.

* cited by examiner

Young +vehicle     Young + TGF-β1     Young + TGF-β1 +OT

FIG. 4B

MOLECULAR COMPOSITION FOR ENHANCING AND REJUVENATING MAINTENANCE AND REPAIR OF MAMMALIAN TISSUES

CROSS REFERENCE TO RELATED APPLICATION

This application is a 371 of U.S. Patent Application Serial No. PCT/US2015/044900, filed on Aug. 12, 2015, which application claims the benefit of U.S. Provisional Patent Application No. 62/036,473, filed Aug. 12, 2014, which application is incorporated herein by reference in its entirety.

GOVERNMENT RIGHTS

This invention was made with government support under contract/grant number AG027252 awarded by the National Institutes of Health. The Government has certain rights in the invention.

INTRODUCTION

As the average world population is aging rapidly, enhancing the elderly quality of life is of major importance for both their well-being and for regulating the associated socioeconomic costs. With aging, the capacity of tissues to regenerate declines and eventually fails, leading to degenerative disorders and eventual organ failure. Sarcopenia affects people over 50 years old and results in a decrease in the level of physical activity causing frailty and disability and the likelihood of falls and fractures. While several treatments that increase muscle mass have been tested to fight this disease, most of them fail in elderly populations and the risk to benefit ratio is so high that exercise is still the primary treatment for the age-specific muscle wasting.

SUMMARY

Methods, pharmaceutical compositions, and kits are provided for treating a subject with an effective amount of an oxytocin receptor (OXTR) agonist and an effective amount of an ALK5 antagonist. In certain aspects, the OXTR agonist may be oxytocin, an oxytocin analog (e.g., carbetocin, demoxytocin, TC OT 39, WAY 267464, or a small molecule). The ALK5 antagonist may be a small molecule, such as A 83-01, D 4476, GW 788388, LY 364947, RepSox, SB 431542, SB 505124, SB 525334, or SD 208. In certain aspects, the amounts of the OXTR agonist and ALK5 antagonist may be sufficient to induce muscle regeneration and enhance neurogenesis, combatting and preventing degenerative disorders in the subject. In certain aspects, the combined administration of the OXTR agonist and ALK5 antagonist may be sufficient to induce muscle regeneration and enhance neurogenesis at a lower effective concentration than that required if only the OXTR agonist or the ALK5 antagonist was administered.

Aspects of the methods disclosed here include enhancing proliferation of a somatic cell. The method may include contacting a somatic cell with oxytocin receptor (OXTR) agonist and ALK5 antagonist, wherein the contacting is with an amount of the OXTR agonist and ALK5 antagonist effective to enhance proliferation of the somatic cell.

The contacting may be in vivo, in vitro, or ex vivo. The somatic cell may be a muscle cell, e.g., a skeletal muscle cell or a myoblast. The somatic cell may be an activated satellite cell. The somatic cell may be a neural cell, e.g., a neural stem cell or a neural progenitor cells. The somatic cell may be an adult human stem or an adult human progenitor cell. The somatic cell may be a cell of an aged subject. The somatic cell may be an injured cell. The injury may be caused by a disease. The somatic cell may be a diseased cell.

In certain aspects the contacting may include administering the OXTR agonist and the ALK5 antagonist to a subject. The subject may be a mammal, for example, a rodent or a primate, e.g., a mouse, rat or a human. The subject may be old or suffering from reduction in muscle mass or neurons, or reduction in other tissues, such as a reduction caused due to natural aging process, injury, extended inactivity, disease, and the like. The subject may be diagnosed as having or susceptible to developing a neurodegenerative disease, such as, Alzheimer's disease, Parkinson's disease, Huntington's disease, or dementia. The subject may be diagnosed as having or susceptible to developing a muscular degeneration. The subject may be suffering from muscular dystrophy due to disease or muscular atrophy due to inactivity associated with an injury or disease.

The amount of the OXTR agonist for the contacting step, e.g., for administering to a subject may be in the range of 7.5 nM-30 nM and the amount of the ALK5 antagonist may be in the range of 0.05 $\mu$M-3 $\mu$M. The ratio of OXTR agonist to the ALK5 antagonist used for contacting step, e.g., for administering to a subject as disclosed herein may be 1:50, 50:1, 1:40, 40:1, 1:30, 30:1, 1:25, 25:1, 1:10, 10:1, 1:5, 5:1, or 1:1.

In certain aspects, the OXTR agonist may be oxytocin. In certain aspects, the ALK5 antagonist may be 2-(3-(6-Methylpyridin-2-yl)-1H-pyrazol-4-yl)-1,5-naphthyridine.

In certain aspects, the proliferation of the somatic cell may be reduced as compared to the proliferation of the same type of somatic cell from a young subject. For example, the somatic cell may be a precursor cell such as a muscle precursor cell or a neural precursor cell.

In certain aspects, the somatic cell may be from a subject who has a disease and the proliferation of the somatic cell may be reduced as compared to the proliferation of the same type of somatic cell from a healthy adult subject. For example, the subject may be a human who has dementia and the proliferation of the hippocampal neural cells may be reduced as compared to hippocampal neural cells of a healthy adult subject.

In certain aspects, the method may further comprising assessing proliferation of the somatic cell following the contacting and adjusting the amount of the OXTR agonist and/or the ALK5 antagonist for the next contacting step.

Contacting may include administering the OXTR agonist and the ALK5 antagonist to a subject. Administering may be systemic or local and may be continuous or on an administration schedule, such as, bi-daily, daily, bi-weekly, weekly, bi-monthly, or monthly.

In certain aspects, the method may further include assessing proliferation of the somatic cell following the contacting and increasing or decreasing the amount of the OXTR agonist.

In certain aspects, the method may further include assessing proliferation of the somatic cell following the contacting and increasing or decreasing the amount of the ALK5 antagonist.

In certain aspects, the method may further include assessing proliferation of the somatic cell following the repeated contacting and adjusting the contacting schedule.

Also provided herein is a composition that includes an OXTR agonist; an ALK5 antagonist; and a pharmaceutically acceptable excipient. The amount of the OXTR agonist may be in the range of 7.5 nM-30 nM and the amount of the ALK5 antagonist may be in the range of 0.05 µM-3 µM. The ratio of the OXTR agonist to the ALK5 antagonist may be 1:50, 50:1, 1:40, 40:1, 1:25, 25:1, 1:10, 10:1, 1:5, 5:1, or 1:1. In certain cases, the OXTR agonist may be oxytocin. In certain cases, the ALK5 antagonist may be 2-(3-(6-Methyl-pyridin-2-yl)-1H-pyrazol-4-yl)-1,5-naphthyridine.

DETAILED DESCRIPTION

Methods, pharmaceutical compositions, and kits are provided for treating a subject with an effective amount of an oxytocin receptor (OXTR) agonist and an effective amount of an ALK5 antagonist. In certain aspects, the OXTR agonist may be oxytocin, an oxytocin analog (e.g., carbetocin, demoxytocin, TC OT 39, WAY 267464), or another small molecule. The ALK5 antagonist may be a small molecule, such as 2-(3-(6-Methylpyridin-2-yl)-1H-pyrazol-4-yl)-1,5-naphthyridine, A 83-01, D 4476, GW 788388, LY 364947, RepSox, SB 431542, SB 505124, SB 525334, or SD 208. In certain aspects, the amounts of the OXTR agonist and ALK5 antagonist may be sufficient to induce muscle regeneration and/or neural cell regeneration in the subject.

Before the present methods and compositions are further described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "treatment", "treating" and the like as used herein refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

An "inhibitor" or "antagonist" as used herein refers to any agent (e.g., small molecule, macromolecule, peptide, etc.) that reduces the activity of an enzyme or receptor. A "Competitive inhibitor" as used herein refers to an inhibitor that reduces binding of a substrate to an enzyme or receptor, such as the binding of a ligand to a sell surface receptor. The competitive inhibitor may specifically bind to the active site of the enzyme or an allosteric site of the enzyme, or may specifically bind the substrate itself. "Non-competitive inhibitor" as used herein refers to an inhibitor that reduces activity of an enzyme regardless of the presence of the substrate. A non-competitive inhibitor may bind to an active site of the enzyme or to an allosteric site of the enzyme.

As used herein, an "oxytocin analog" refers to a peptide having a similar amino acid sequence to oxytocin, with one or more amino acid substitutions, unnatural amino acids, side chain modifications, or any other suitable modification.

The terms "individual," "subject," "host," and "patient," are used interchangeably herein and refer to any mammalian subject for whom diagnosis, treatment, or therapy is desired, particularly humans.

The terms "specific binding," "specifically binds," and the like, refer to the preferential binding of a binding element (e.g., one binding pair member to the other binding pair member of the same binding pair) relative to other molecules or moieties in a solution or reaction mixture. The binding element may specifically bind (e.g., covalently or non-covalently) to a particular epitope or narrow range of epitopes within the cell. In certain aspects, the binding element non-covalently binds to a target.

The term "effective amount" as used herein refer to the amount of an agent (e.g., dosage, concentration in plasma, etc.) that elicits a desired biological effect, such as enhancing or suppressing the signaling of a cell surface receptor (e.g., OXTR or ALK5) or inducing tissue regeneration (e.g., muscle regeneration). Effective amounts may readily be determined empirically from assays, from safety and escalation and dose range trials, individual clinician-patient relationships, as well as in vitro and in vivo assays such as those described in the art.

By "IC50" is intended the concentration of an antagonist required to achieve 50% inhibition of a specific biological or biochemical function, such as ALK5 signaling. By "EC50" is intended the plasma concentration required for obtaining 50% of a maximum biological effect.

The term "sarcopenia" as used herein refers to the degenerative loss of skeletal muscle mass and/or strength, and is associated with aging. In contrast, "muscle regeneration" as used herein refers to the increase in muscle (e.g., skeletal muscle) mass or strength upon treatment.

The term "neurogenesis" as used herein refers to the generation of new neurons in adult mammalian brain (primarily, but not exclusively, in hippocampus, region of brain responsible for learning and memory).

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

OXTR Agonists

The oxytocin receptor (OXTR) is a G-protein coupled receptor for the peptide oxytocin, which acts a hormone and neurotransmitter. Oxytocin is FDA approved and sold under the name of Pitocin and Syntocinon. Aspects of the invention include an OXTR agonist (such as oxytocin) or the use thereof.

An OXTR agonist is any agent that specifically enhances OXTR expression, OXTR signaling, or signaling downstream of the OXTR. In certain aspects, the OXTR agonist may include oxytocin (e.g., Pitocin, Syntocinon or generic oxytocin) or an oxytocin mimetic, i.e., a peptide having a similar amino acid sequence to oxytocin, one or more amino acid substitutions, unnatural amino acids, or any other suitable modification. An oxytocin analog of the subject invention may be 8 or 9 amino acids in length. An oxytocin analog may have one or more, two or more, three or more, or four or more chemical modifications as compared to oxytocin.

Examples of oxytocin analogs that act as OXTR agonists include Demoxytocin, Carbetocin, TC OT 39 and WAY-267464 (e.g., WAY-267464 dihydrochloride), or a derivative thereof. Demoxytocin (also known as Sandopart or deaminooxytocin) is an analogue of oxytocin, and an OXTR agonist. Demoxytocin has an IUPAC name of 2-[(1-{[13-(butan-2-yl)-10-(2-carbamoylethyl)-7-(carbamoylmethyl)-16-[(4-hydroxyphenyl)methyl]-6,9,12,15,18-pentaoxo-1,2-dithia-5,8,11,14,17-pentaazacycloicosan-4-yl]carbonyl}pyrrolidin-2-yl)formamido]-N-(carbamoylmethyl)-4-methylpentanamide and a Chemical Abstracts Service registry number (CAS number) of 113-78-0. Carbetocin (also known as Duratocin, Pabal, Lonactene) is an eight amino acid long oxytocin analogue that primarily agonizes peripherally expressed oxytocin receptors. Carbetocin has an IUPAC name of (2S)-1-[(3S, 6S,9S,12S,15S)-12-[(2S)-butan-2-yl]-9-(2-carbamoylethyl)-6-(carbamoylmethyl)-15-[(4-hydroxyphenyl)methyl]-16-methyl-5,8,11,14,17-pentaoxo-1-thia-4,7,10,13,16-pentazacycloicosane-3-carbonyl]-N-[(1S)-1-(carbamoylmethylcarbamoyl)-3-methyl-butyl]pyrrolidine-2-carboxamide and a CAS number of 37025-55-1. TC OT 39 is a non-peptide oxytocin analog and partial agonist of OXTR and vasopressin V2 receptors. TC OT 39 has an IUPAC name of (2S)—N-[[4-[(4,10-Dihydro-1-methylpyrazolo[3,4-b][1,5]benzodiazepin-5(1H)-yl)carbonyl]-2-methylphenyl]methyl]-2-[(hexahydro-4-methyl-1H-1,4-diazepin-1-yl)thioxomethyl]-1-pyrrolidinecarboxamide and a CAS number of 479232-57-0. WAY-267464 is a non-peptide oxytocin analogue and OXTR agonist with minimal affinity for vasopressin receptors. WAY-267464 has an IUPAC name of 4-(3,5-dihydroxybenzyl)-N-(2-methyl-4-[(1-methyl-4,10-dihydropyrazolo[3,4-b][1,5]benzodiazepin-5(1H)-yl)carbonyl]benzyl)piperazine-1-carboxamide and a CAS number of 847375-16-0.

In certain aspects, the OXTR agonist may be a small molecule. For example, the OXTR agonist may be 1 kDa or less, 900 Da or less, 800 Da or less, 700 Da or less, 600 Da or less, 500 Da or less, 400 Da or less, 300 Da or less, 200 Da or less, or 100 Da or less. Small molecule compounds may be dissolved in water or alcohols or solvents such as DMSO or DMF, and diluted into water or an appropriate buffer prior to being provided to cells. The OXTR agonist may optionally include a moiety preventing transport across the blood brain barrier (BBB).

OXTR agonists are well known in the art, as evidenced by U.S. Pat. No. 8,748,564 and US Publication Nos. US20070117794 and US20130085106, the disclosures of which are incorporated herein by reference.

In certain aspects, the OXTR agonists may include an OXTR specific binding member. The terms "specific binding," "specifically binds," and the like, refer to the preferential binding of a domain (e.g., one binding pair member to the other binding pair member of the same binding pair) relative to other molecules or moieties in a solution or reaction mixture. The binding domain may specifically bind (e.g., covalently or non-covalently) to a particular epitope or narrow range of epitopes within the cell. In such instances, the OXTR specific binding member association with OXTR may be characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less.

A variety of different types of specific binding members may be employed. Binding members of interest include, but are not limited to, antibodies, proteins, peptides, haptens, nucleic acids, aptamers, etc. In certain aspects, the OXTR specific binding member may be an antibody or a fragment thereof. The term "antibody" as used herein includes polyclonal or monoclonal antibodies or fragments thereof that are sufficient to bind to an analyte of interest. The fragments can be, for example, monomeric Fab fragments, monomeric Fab' fragments, or dimeric F(ab)'2 fragments. Also within the scope of the term "antibody" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In certain embodiments, the OXTR agonist may be an agent that modulates, e.g., enhances, expression of functional OXTR. OXTR expression may be enhanced using any convenient means, including use of an agent that enhances OXTR expression, such as, but not limited to vectors (e.g., plasmids, retroviruses, etc.) encoding functional OXTR under an inducible promoter, tissue specific promoter, or may be constitutively expressed.

ALK5 Antagonists

Activin A receptor type II-like kinase (ALK5), also known as transforming growth factor beta receptor I (TGF-β receptor), is a serine/threonine kinase receptor expressed in a variety of tissues. Alk5 inhibitors are undergoing several clinical trials for treating cancers and attenuating metastasis. Certain aspects of the invention include an ALK5 antagonist (i.e., an ALK5 inhibitor) or the use thereof.

An ALK5 antagonist is any agent that specifically reduces OXTR expression, ALK5 signaling, or signaling downstream of the OXTR. Examples of ALK5 agonists include competitive inhibitors and non-competitive inhibitors. An ALK5 agonist may bind TGF-β or the TGF-β receptor.

In certain aspects, the ALK5 antagonist may be a small molecule. For example, the ALK5 antagonist may be 1 kDa or less, 900 Da or less, 800 Da or less, 700 Da or less, 600 Da or less, 500 Da or less, 400 Da or less, 300 Da or less, 200 Da or less, or 100 Da or less. Small molecule compounds may be dissolved in water or alcohols or solvents such as DMSO or DMF, and diluted into water or an appropriate buffer prior to being provided to cells. The small molecule may be a competitive inhibitor of ALK5-TGF-β binding or a non-competitive inhibitor of ALK5 activity.

Examples of ALK5 antagonists include 2-(3-(6-Methyl-pyridin-2-yl)-1H-pyrazol-4-yl)-1,5-naphthyridine, galunisertib (LY2157299 monohydrate), A 83-01, D 4476, GW 788388, LY 364947, RepSox, SB 431542, SB 505124, SB 525334, and SD 208, or a derivative thereof. A 83-01 is a selective inhibitor of ALK4, ALK5 and ALK7. A 83-01 has an IUPAC name of 3-(6-Methyl-2-pyridinyl)-N-phenyl-4-(4-quinolinyl)-1H-pyrazole-1-carbothioamide and a Chemical Abstracts Service registry number (CAS number) of 909910-43-6. D 4476 is an inhibitor of ALK5 and CK1. D 4476 has an IUPAC name of 4-[4-(2,3-Dihydro-1,4-benzo-dioxin-6-yl)-5-(2-pyridinyl)-1H-imidazol-2-yl]benzamide and a CAS number of 301836-43-1. GW 788388 is a selective inhibitor of ALK5. GW 788388 has an IUPAC name of 4-[4-[3-(2-Pyridinyl)-1H-pyrazol-4-yl]-2-pyridinyl]-N-(tetrahydro-2H-pyran-4-yl)-benzamide and a CAS number of 452342-67-5. LY 364947 (also known as HTS 466284) is a selective inhibitor of ALK5. LY 364947 has an IUPAC name of 4-[3-(2-Pyridinyl)-1H-pyrazol-4-yl]-quinoline and a CAS number of 396129-53-6. RepSox (also known as E-616452 and SJN 2511) is a selective inhibitor of ALK5. RepSox has an IUPAC name of 2-(3-(6-Methylpyridine-2-yl)-1H-pyrazol-4-yl)-1,5-naphthyridine and a CAS number of 446859-33-2. SB 431542 is a selective inhibitor of ALK4, ALK5 and ALK7. SB 431542 has an IUPAC name of 4-[4-(1,3-benzodioxol-5-yl)-5-(2-pyridinyl)-1H-imidazol-2-yl]benzamide and a CAS number of 301836-41-9. SB 505124 is a selective inhibitor of ALK4, ALK5 and ALK7. SB 505124 has an IUPAC name of 2-[4-(1,3-Benzodioxol-5-yl)-2-(1,1-dimethylethyl)-1H-imidazol-5-yl]-6-methyl-pyridine and a CAS number of 694433-59-5. SB 525334 is a selective inhibitor of ALK5. SB 525334 has an IUPAC name of 6-[2-(1,1-Dimethylethyl)-5-(6-methyl-2-pyridinyl)-1H-imidazol-4-yl]quinoxaline and a CAS number of 356559-20-1. SD 208 is an ATP-competitive ALK5 inhibitor. SD 208 has an IUPAC name of 2-(5-Chloro-2-fluoro-phenyl)-4-[(4-pyridyl)amino]pteridine and a CAS number of 627536-09-8.

ALK5 antagonists are well known in the art, as evidenced by US Publication Nos. US20060194845, US20050245520, and US20040266842, the disclosures of which are incorporated herein by reference.

In certain aspects, the ALK5 antagonists may include an ALK5 specific binding member. The terms "specific binding," "specifically binds," and the like, refer to the preferential binding of a domain (e.g., one binding pair member to the other binding pair member of the same binding pair) relative to other molecules or moieties in a solution or reaction mixture. The binding domain may specifically bind (e.g., covalently or non-covalently) to a particular epitope or narrow range of epitopes within the cell. In such instances, the ALK5 specific binding member association with ALK5 may be characterized by a KD (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less.

A variety of different types of specific binding members may be employed. Binding members of interest include, but are not limited to, antibodies, proteins, peptides, haptens, nucleic acids, aptamers, etc. In certain aspects, the ALK5 specific binding member may be an antibody or a fragment thereof. The term "antibody" as used herein includes polyclonal or monoclonal antibodies or fragments thereof that are sufficient to bind to an analyte of interest. The fragments can be, for example, monomeric Fab fragments, monomeric Fab' fragments, or dimeric F(ab)'2 fragments. Also within the scope of the term "antibody" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In certain embodiments, the ALK5 antagonist may be an agent that modulates, e.g., inhibits, expression of functional ALK5. Inhibition of ALK5 expression may be accomplished using any convenient means, including use of an agent that inhibits ALK5 expression, such as, but not limited to: antisense agents, RNAi agents, agents that interfere with transcription factor binding to a promoter sequence of the ALK5 gene, or inactivation of the ALK5 gene, e.g., through recombinant techniques, etc.

For example, antisense molecules can be used to down-regulate expression of ALK5 in the cell. The anti-sense reagent may be antisense oligodeoxynucleotides (ODN), such as synthetic ODN having chemical modifications from native nucleic acids, nucleic acid constructs that express such anti-sense molecules as RNA, and so forth. The anti-sense sequence may be complementary to the mRNA of the targeted protein (i.e., ALK5). Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule may be a synthetic oligonucleotide. Antisense oligonucleotides may be at least 7 nucleotides in length, at least 10 nucleotides in length, at least 15 nucleotides in length, at least 20 nucleotides in length, 500 or fewer nucleotides in length, 100 or fewer nucleotides in length, 50 or fewer nucleotides in length, 25 or fewer nucleotides in length, between 7 and 50 nucleotides in length, between 10 and 25 nucleotides in length, and so forth, where the length is governed by efficiency of inhibition, specificity, including absence of cross-reactivity, and the like.

A specific region or regions of the endogenous sense strand mRNA sequence may be chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5-O-phosphorothioate, 3'-CH$_2$-5'-O-phosphonate and 3'-NH-5-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res*. 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol*. 54:43-56.

In addition, the transcription level of an ALK5 can be regulated by gene silencing using RNAi agents, e.g., double-strand RNA (Sharp (1999) *Genes and Development* 13: 139-141). RNAi, such as double-stranded RNA interference (dsRNAi) or small interfering RNA (siRNA), has been extensively documented in the nematode *C. elegans* (Fire, A., et al, *Nature*, 391, 806-811, 1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

Methods of Treatment

Aspects of the invention are directed to a method of treating a subject. The method may include administering an oxytocin receptor (OXTR) agonist and an ALK5 antagonist to the subject. As described above, the OXTR agonist may be any agent that specifically enhances OXTR expression, OXTR signaling, or signaling downstream of the OXTR and the ALK5 antagonist may be any agent that specifically reduces ALK5 expression or ALK5 signaling. In certain aspects the OXTR agonist may be oxytocin. In certain aspects the ALK5 antagonist may be galunisertib (LY2157299 monohydrate). The amount of the OXTR agonist and ALK5 antagonist administered in the subject methods may be effective to achieve any of a number of desired outcomes, as discussed below.

A combination of oxytocin (or another OXTR agonist) with Alk5 inhibitor is expected to potentiate the positive effects on muscle, bone, combat age-related fat deposition and promote and rejuvenate hippocampal neurogenesis (leading to increase in memory and cognition and preventing loss of memory and cognition in the elderly).

The amount of the OXTR agonist and ALK5 antagonist may therefore be effective to enhance fat distribution, prevent or reduce weight gain after menopause, treat or prevent osteoporosis, enhance wound healing, enhance cognition, reduce memory loss, enhance liver regeneration, restore productive hematopoiesis and/or broadly improve tissue maintenance and repair in an elderly subject. Unlike many other substances that are postulated to enhance tissue regeneration, oxytocin is not associated with cancers, e.g. is not oncogenic and Alk5 inhibitors are in fact anti-oncogenic and are in clinical trials for suppressing metastasis (Inman, G. J. (2011). Switching TGFbeta from a tumor suppressor to a tumor promoter. Current opinion in genetics & development 21, 93-99.). Thus, a combination of oxytocin (or another OXTR agonist) with Alk5 inhibitor will be used to improve the health of multiple tissues, particularly, in the elderly, while minimizing the side effects associated with oncogenesis. The same combination may also be used to promote regeneration of tissue after injury in younger patients.

In certain aspects, the amount of the OXTR agonist and ALK5 antagonist may be effective to treat sarcopenia, promote muscle regeneration (e.g., after injury, after long term immobilization (e.g., due to bed rest, cast, coma), after stroke, after or upon exposure to low gravity, etc.), and/or to prevent muscle loss and cachexia developed with aging or long term immobility. Alternatively or in addition, the amount of the OXTR agonist and ALK5 antagonist may be effective to attenuate persistent, excessive inflammation, such as is seen in arthritic, certain auto-immune diseases, and severe trauma.

In certain aspects, the amount of the OXTR agonist and ALK5 antagonist may be effective to prevent or treat age related cosmetic changes. For example, the amount of the OXTR agonist and ALK5 antagonist may be effective to prevent or treat wrinkles, prevent hair loss, promote hair regrowth, etc.

Effective amounts of the OXTR agonist and/or ALK5 antagonist may readily be determined empirically from assays, from safety and escalation and dose range trials, individual clinician-patient relationships, as well as in vitro and in vivo assays such as those described in the art (e.g., Reagan-Shaw et al. (2007) The FASEB Journal 22:659-661).

The subject may be any suitable animal, such as a rodent (e.g., mouse, rat, etc.), primate (e.g., human, monkey, etc.), and so forth. In one embodiment, the subject may be a mouse. In certain embodiments, the subject may be a human. The subject may have sarcopenia, muscle injury, cachexia, arthritis, an auto-immune disease, severe trauma, osteoporosis, obesity and related metabolic disorders, or any disease involving degeneration of tissue. In certain aspects, subject may be elderly, e.g., 60 years or older, 65 years or older, 70 years or older, 75 years or older, 80 years or older, 85 years or older, 90 years or older, and so forth. The subject may be a male or a female subject.

The OXTR agonist and ALK5 antagonist may be administered by any suitable route of administration, such as by enteric administration (e.g., oral) or by parenteral administration (e.g., intravenous, intra-arterial, intra-muscular, subcutaneous, etc.). For example, the OXTR agonist and ALK5 antagonist may be delivered by daily injections, nasal spray, using pump, delivered topically as a cream or using patches, oral tablets that prevent degradation of these bioactive molecules by the gastrointestinal tract. In addition, the OXTR agonist and/or ALK5 antagonist may be incorporated into a variety of formulations for therapeutic administration, according to any of the embodiments discussed herein. In certain cases, the OXTR agonist and ALK5 antagonist may be administered directly into a location in the body, such as, injured muscle, bone, a region of the brain (e.g., hippocampus), and the like.

In certain embodiments, the amount of an ALK5 antagonist to be administered may be gauged from the IC50 of the given ALK5 antagonist. By "IC50" is intended the concentration of an antagonist required to achieve 50% inhibition of a specific biological or biochemical function, such as ALK5 signaling.

With respect to the ALK5 antagonists of the present disclosure, an effective amount (e.g., the amount to be administered) may be 200× the calculated IC50 or less. For example, the amount (e.g., effective amount, amount to be administered, etc.) of an OXTR agonist and/or ALK5 antagonist may be 200× or less, 150× or less, 100× or less, 75× or less, 60× or less, 50× or less, 45× or less, 40× or less, 35× or less, 30× or less, 25× or less, 20× or less, 15× or less, 10× or less, 8× or less, 5× or less, 2× or less, 1× or less, 0.5× or less, or 0.25× or less than the calculated IC50. In one embodiment, the effective amount may be 1× to 100×, 2× to 40×, 5× to 30×, or 10× to 20× of the calculated IC50.

With respect to OXTR agonists and ALK5 antagonists of the present disclosure, the effective amount (amount to be administered) may be gauged from the EC50. By "EC50" is intended the plasma concentration required for obtaining 50% of a maximum biological effect. Suitable biological effects include binding of the OXTR agonist to OXTR, binding of the ALK5 antagonist to ALK5, OXTR agonist effect on OXTR signaling, ALK antagonist effect on ALK5 signaling, and/or downstream effects such as cell regeneration. An effective amount may be 200× the calculated EC50 or less. The amount (e.g., effective amount, amount to be administered, etc.) of an OXTR agonist and/or ALK5 antagonist may be 200× or less, 150× or less, 100× or less, 75× or less, 60× or less, 50× or less, 45× or less, 40× or less, 35× or less, 30× or less, 25× or less, 20× or less, 15× or less, 10× or less, 8× or less, 5× or less, 2× or less, 1× or less, 0.5× or less, or 0.25× or less than the calculated EC50. In one embodiment, the effective amount may be 1× to 100×, 2× to 40×, 5× to 30×, or 10× to 20× of the calculated EC50.

The OXTR agonist and ALK5 antagonist may exhibit a synergistic effect. As such, the effective amounts of the OXTR agonist and ALK5 antagonist may be less, e.g., half as much or less, than the effective amount of either agent alone.

Targeting and calibrating to healthy levels of distinct pathways (MAPK by OXTR agonist and TGF-beta by Alk5 antagonist) may promote a broad improvement in function of most mammalian cells, because MAPK and TGF-β signaling are the key cell-fate regulators.

In certain aspects, the OXTR agonist may be oxytocin administered by infusion or by local injection, e.g., by intravenous infusion at a rate of 0.01 µg/h to 100 µg/h, including 0.1 µg/h to 10 µg/h, 0.5 µg/h to 5 µg/h, etc. Administration (e.g., by infusion) can be repeated over a desired period, e.g., repeated over a period of 1 day to 5 days or once every several days, for example, five days, over 1 month, 2 months, etc. It also can be administered prior, at the time of, or after other therapeutic interventions. Alternatively, oxytocin may be administered by intramuscular injection, e.g., at an amount of 0.1 μg to 1000 μg, including 1 μg to 100 μg, 5 μg to 50 μg, 10 μg to 30 μg etc.

In certain aspects, a method for enhancing proliferation of a somatic cell is provided. The method may include contacting the somatic cell with oxytocin receptor (OXTR) agonist and ALK5 antagonist, where the contacting is with an amount of the OXTR agonist and ALK5 antagonist effective to enhance proliferation of the somatic cell, where the contacting is for a period of time sufficient to provide for enhanced proliferation of the somatic cell compared to the absence of the OXTR agonist and ALK5 antagonist. In certain aspects, the combined administration of the OXTR agonist and ALK5 antagonist provides a synergistic effect where the effective amounts the OXTR agonist and ALK5 antagonist is lesser that the amount required to enhance proliferation of the somatic cell when the somatic cell is contacted with either the OXTR agonist or the ALK5 antagonist.

In certain aspects, the effective amount of the OXTR agonist when administered in combination with the ALK5 antagonist may be 10% less, 20% less, 30% less, 40% less, 50% less, 60% less, or lesser than the amount of the OXTR agonist required to achieve the same effect when administered in absence of the ALK5 antagonist. In certain aspects, the effective amount of the ALK5 antagonist when administered in combination with the OXTR agonist may be 10% less, 20% less, 30% less, 40% less, 50% less, 60% less, or lesser than the amount of the ALK5 antagonist required to achieve the same effect when administered in absence of the OXTR agonist. Thus, the combined administration of the OXTR agonist and the ALK5 antagonist allows lowering the doses of each molecule, thus not skewing the respective pathways far from healthy signaling ranges, while maintaining and/or even broadening the positive effects on multiple tissues and their stem cells.

In certain aspects the combined administration of the OXTR agonist and the ALK5 antagonist may enhance proliferation of a somatic cell (e.g., myogenic or neurogenic cell) by at least 10% more, 20% more, 30% more, 40% more, 50% more, 60% more, or more than the proliferation affected by either molecule alone.

In certain aspects the combined contacting with the OXTR agonist and the ALK5 antagonist may enhance proliferation of a somatic cell (e.g., myogenic or neurogenic cell) by at least 10% more, 20% more, 30% more, 40% more, 50% more, 60% more, or more than the proliferation of the same type of somatic cell in absence of the contacting.

In certain cases, the effective concentration of the ALK5 antagonist (e.g., Galunisertib (LY2157299)) may be 0.05 μM-0.75 μM and the effective concentration of the OXTR agonist (e.g., oxytocin) may be 7.5 nM-30 nM for enhancing proliferation of myoblasts. In certain cases, the effective concentration of the ALK5 antagonist (e.g., Galunisertib (LY2157299)) may be 0.5 μM-3 μM and the effective concentration of the OXTR agonist (e.g., oxytocin) may be 10 nM-30 nM for enhancing proliferation of satellite cells of an old subject.

In certain aspects, the effective concentration of oxytocin may be in the range of 0.01 to 1 microgram per gram mouse body weight per day. In certain aspects, oxytocin may be administered by intraperitoneal or subcutaneous injection, or continually by osmotic pump. In certain aspects, the effective concentration of the ALK5 antagonist (e.g., 2-(3-(6-Methylpyridin-2-yl)-1H-pyrazol-4-yl)-1,5-naphthyridine) may be in the range of 2 to 200 picomoles per gram mouse body weight per day. In certain aspects, the ALK5 antagonist may be administered by intramuscular, intraperitoneal or subcutaneous injection, or continually by osmotic pump.

The effective concentrations of the OXTR agonist and ALK5 antagonist for a human subject may be extrapolated from effective concentrations derived from animal studies. For example, the following conversion table may be used for determining human equivalent dose:

TABLE 1

Conversion of Animal Doses to Human Equivalent Doses Based on Body Surface Area

| Species | To Convert Animal Dose in mg/kg to Dose in mg/m², Multiply by $k_m$ | To Convert Animal Dose in mg/kg to HED[a] in mg/kg, Either: | |
|---|---|---|---|
| | | Divide Animal Dose By | Multiply Animal Dose By |
| Human | 37 | — | — |
| Child (20 kg)[b] | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula: HED = animal dose in mg/kg × (animal weight in kg/human weight in kg)$^{0.33}$.
[b]This $k_m$ value is provided for reference only since healthy children will rarely be volunteers for phase 1 trials.
[c]For example, cynomolgus, rhesus, and stumptail.

As noted above, the somatic cell may be a muscle cell, such as, a skeletal muscle cell, cardiac muscle cell, or a myoblast. In certain aspects, the somatic cell may be a precursor cell such as a satellite cell (e.g., Pax7+Myf5+ satellite cells), muscle stem cell, neural stem cell (e.g., Sox-2+ Doublecortin+ hippocampal subgranular zone (SGZ) cells), and the like. In certain aspects the somatic cell may be an activated satellite cell or a neural cell.

The somatic cell may be a cell of an aged subject as noted above and/or an injured cell. The injury may be caused by either a disease or due to a physical injury.

The contacting maybe in vivo, in vitro, or ex vivo. In certain aspects, the contacting is performed in vitro. For example, the somatic cell may be cultured in a low mitogen medium and contacted with both the OXTR agonist and the ALK5 antagonist to enhance proliferation of the somatic cell. In certain aspects, the somatic cell may be a liver cell. In certain aspects, the somatic cell may be albumin+Ki67+ hepatocytes. In other aspects, the contacting includes administering the OXTR agonist and the ALK5 antagonist to a subject in need thereof.

In certain aspects, a somatic cell may be isolated from a subject, and contacted with the OXTR agonist and the ALK5 antagonist to enhance proliferation of the somatic cell and the proliferated somatic cells may be administered to the subject. The proliferated somatic cells may be transplanted to a particular location in the subject, such as, muscle, spinal cord, brain, bone, lover, pancreas and the like.

The treatment methods may also include an assessment of proliferation of the somatic cell following the contacting with the OXTR agonist and the ALK5 antagonist. Based on the assessed proliferation or lack thereof, the amounts of the OXTR agonist and/or the ALK5 antagonist may be adjusted by increasing or decreasing the amounts and/or the schedule of administration of the OXTR agonist and the ALK5 antagonist.

In certain aspects, the method may include contacting the somatic cell with only one of the OXTR agonist and the ALK5 antagonist prior to or after contacting the somatic cell with both the OXTR agonist and the ALK5 antagonist.

Pharmaceutical Composition

Aspects of the invention are directed to pharmaceutical compositions for treatment of a subject. The pharmaceutical compositions may include an OXTR agonist and an ALK5 antagonist. As described above, the OXTR agonist may be any agent that specifically enhances OXTR expression, OXTR signaling, or signaling downstream of the OXTR and the ALK5 antagonist may be any agent that specifically reduces OXTR expression, ALK5 signaling, or signaling downstream of the OXTR.

The OXTR agonist and ALK5 antagonist may each be present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g., liposomes, e.g., liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the composition can be achieved in various ways, including transdermal, intradermal, oral, buccal, rectal, parenteral, intraperitoneal, intradermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

The pharmaceutical composition may further include a pharmaceutically acceptable carrier. The OXTR agonist and ALK5 may (together or separately) be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, the pharmaceutical composition may be suitable for administration in various ways, including oral, buccal, rectal, parenteral, intraperitoneal, intradermal, transdermal, intracheal, etc., administration.

Preparations of the pharmaceutical composition may be sterile. Sterility is readily accomplished by filtration through sterile filtration membranes (e.g., 0.2 µm membranes). Therapeutic compositions may be placed into a container having a sterile access port, for example, an intravenous solution bag or vial having a stopper pierceable by a hypodermic injection needle. The pharmaceutical composition may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution may be prepared by reconstituting the lyophilized compound using bacteriostatic Water-for-Injection. Alternatively, the therapeutic moiety may be formulated into lotions for topical administration.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent may be selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990). The components used to formulate the pharmaceutical compositions may be of high purity and are substantially free of potentially harmful contaminants (e.g., at least National Food (NF) grade, at least analytical grade, at least pharmaceutical grade). Moreover, compositions intended for in vivo use may be sterile.

The pharmaceutical composition can be incorporated into a variety of formulations. More particularly, the therapeutic moiety may be formulated into pharmaceutical compositions by combination with appropriate pharmaceutically acceptable carriers or diluents.

Kits

Aspects of the invention include a kit for treatment of a subject. The kit may include an OXTR agonist and an ALK5 antagonist in pharmaceutically acceptable vehicles as described above. The OXTR agonist and ALK5 antagonist may each be present in solid, semi-solid, liquid or gaseous forms, such as tablets, capsules, powders, granules, ointments, solutions, suppositories, injections, inhalants and aerosols. As such, the pharmaceutical composition may be suitable for administration in various ways, including oral, buccal, rectal, parenteral, intraperitoneal, intradermal, transdermal, intracheal, etc., administration.

In addition to the above components, the subject kits may further include instructions for practicing the subject methods. These instructions may be present in the subject kits in a variety of forms, one or more of which may be present in the kit. One form in which these instructions may be present as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the internet to access the information at a removed site.

Utility

OXTR agonists may be used to treat and prevent sarcopenia, improve muscle regeneration after injury and prevent muscle mass loss observed after long term immobilization (bed rest or cast), as well as low gravity (space travel). Specifically, oxytocin is more desirable than other drugs on the market or under development, since it is physiologic, has virtually no side effects and is already FDA approved to induce labor in pregnant women and in clinical trials to treat children with autism. The plasmatic level of oxytocin decreases with age in mice. A short term subcutaneous injection (systemic delivery) of oxytocin is able to restore muscle regeneration in old mice and conversely, the injection of an oxytocin antagonist in young mice prematurely ages their muscle regeneration potential (see Elabd et al. (2014) *Nature Communications* 5:4082). Confirming the dependence of muscle maintenance and repair on oxytocin, mice with a knock out in oxytocin have defective muscle regeneration and premature sarcopenia (loss of muscle tissue). Oxytocin is also known to prevent osteoporosis and regulate fat distribution after menopause. Oxytocin inhibits p16 (marker and effector of senescence) in adult stem cells, thereby enabling their productive responses to maintain and repair tissues. The positive effects of oxytocin can be further supplemented by the small molecule inhibitor of TGF-beta receptor (ALK5 inhibitor), which simultaneously rejuvenates myogenesis and neurogenesis and reduces inflammation, when delivered systemically into 2-year old mice (equivalent of ~85 year old human).

Summarily, systemic delivery of oxytocin and Alk5 inhibitor is capable of combating and reversing the aging of multiple tissues, including muscle, brain and bone and is effective in down-modulating cellular senescence, reducing inflammation and reducing obesity (known to be associated with and exacerbate metabolic disorders). The mixture of these two molecules enables the long-term applications, in which each drug is not used at a high dose, therefore, the negative effects of down-regulation of TGFβ signaling and/or up-regulation of MAPK/pERK signaling are minimized, while the positive effects on health, maintenance and repair of multiple tissues and organs are maximized and/or optimal.

A combination of oxytocin (or another OXTR agonist) with Alk5 inhibitor may be used to potentiate the positive effects on muscle, bone, combat age-related fat deposition and to promote and rejuvenate hippocampal neurogenesis (leading to increase in memory and cognition and preventing loss of memory and cognition in the elderly).

EXAMPLES

Example 1: Alk5i and Oxytocin Enhance Proliferation of Muscle and Neural Cells

Figure 1:
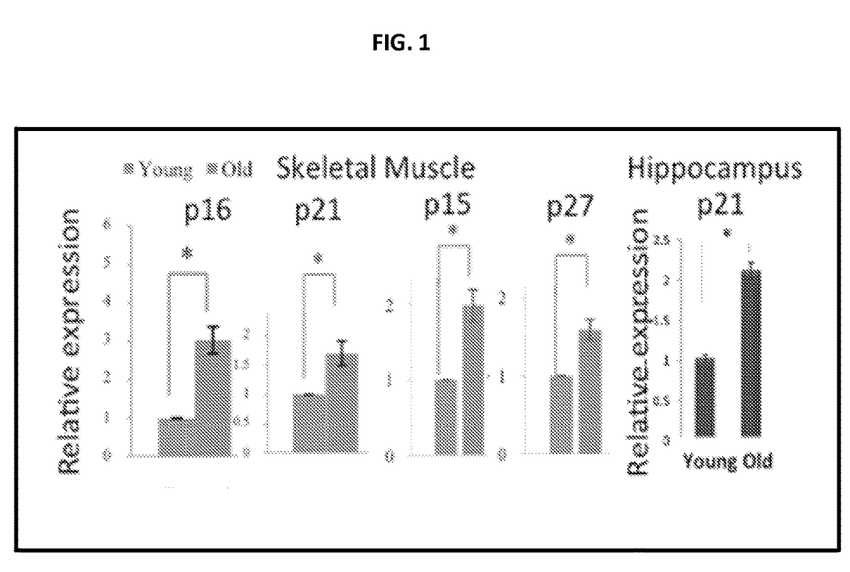
FIG. 1 shows that CDK inhibitors (CDKIs) increase with age in muscle stem cells and neural stem cells.

CDK inhibitors (CDKIs) become up regulated with age in the satellite cells and in SGZ cells (FIG. 1). Such increase is in part due to the age-elevated TGF-beta/pSmad2, 3 in both muscle stem cells and in the Sox-2+ neural SGZ stem cells. Accordingly, Alk5i attenuates the expression of CDKIs and enhances myogenesis and neurogenesis in the aged mice; systemically administered Alk5i has central effects down-modulating pSmads in Sox-2+ cells of SGZ.

FIG. 1. CDKIs increase with age in muscle stem cells and neural stem cells. Age-specific up regulation of CDKIs in muscle stem cells at 3 DPI and in hippocampal SGZ cells (studied by qRT PCR). The levels of p21 are also increased in quiescent old muscle stem cells where p16, p21 loci are more open epigenetically in the old cells, as compared to young cells, and CDKI proteins are also elevated with age in satellite cells. Young cells (left bar); old cells (right bar).

Figure 2A:
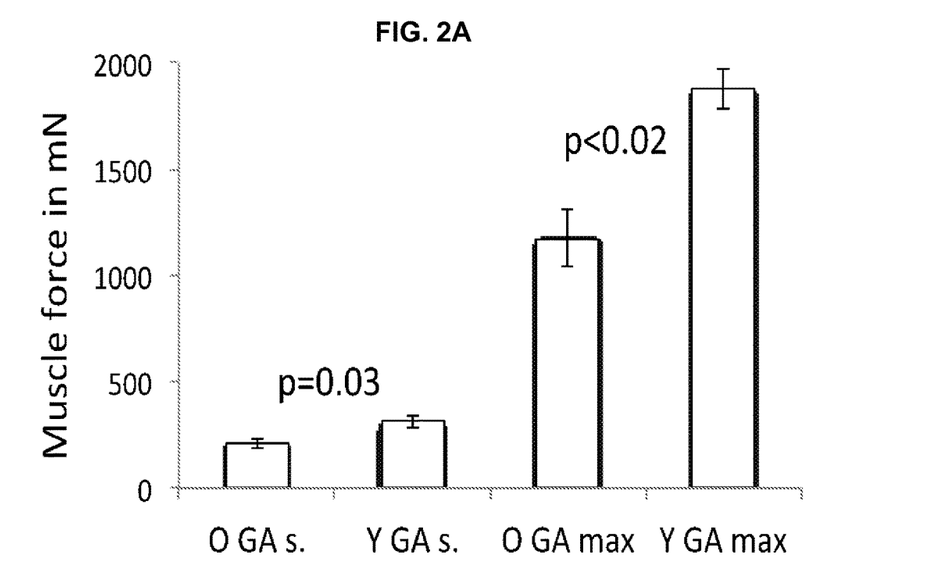
FIGS. 2A and 2B show that muscle strength and lean body mass decline, while body fat increases with age in mice.
Figure 2B:
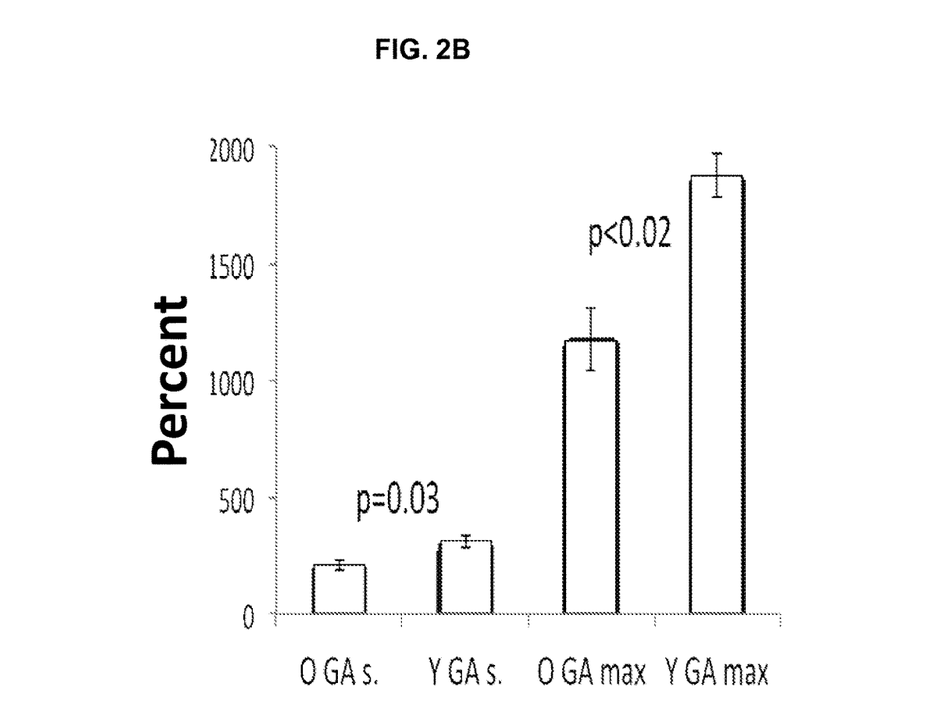

Age-related decline in myogenesis is accompanied by decrease in muscle strength and lean mass (FIGS. 2A and 2B). FIG. 2A. Gasctroc muscle (GA) was dissected at the distal tendon (Achilles) and contractile forces, single twitch (s) and maximal tetanic force (max), were measured under electro-stimulation at the Sciatic nerve. Shown are mean values for young (Y, 3 mo, 4 mice) and old (O, 23 mo, 8 mice), +/−S.E.M. with p-values shown. FIG. 2B. Percent body fat and lean mass 2-4 month and 12-20 month, B6129S mice were measured live by quantitative magnetic resonance (EchoMRI 100H, Houston, Tex.). Shown are mean %+/− S.E.M. *p<0.05 n=5-9.

The correlation between the decline in muscle stem cell responses and loss of muscle size, fiber diameter and accumulation of fat is also evident in the oxytocin knock out (OtKO) mice at 1 year of age; oxytocin (OT) rescues the OtKO satellite cell decline. OT activates pERK in muscle stem cells, attenuates CDKIs enhances proliferation and myogenicity of the old satellite cells, while OTA inhibits myogenicity of the young satellite cells.

Figure 3A:
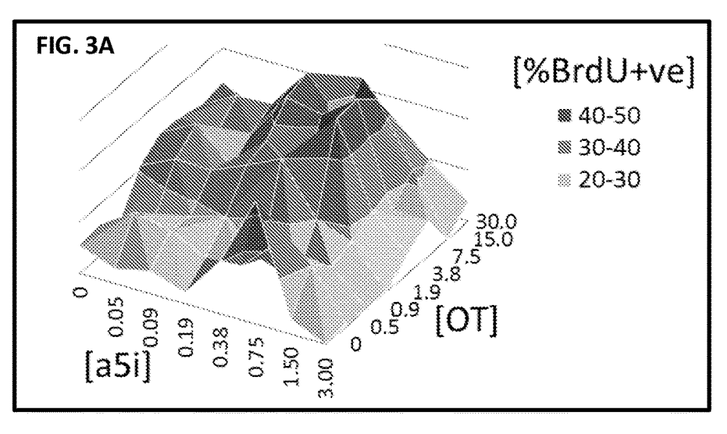
FIGS. 3A-3C depict dose-curve matrix of effects OT, Alk5i and OT+Alk5i on myogenic and neurogenic cell proliferation.
Figure 3B:
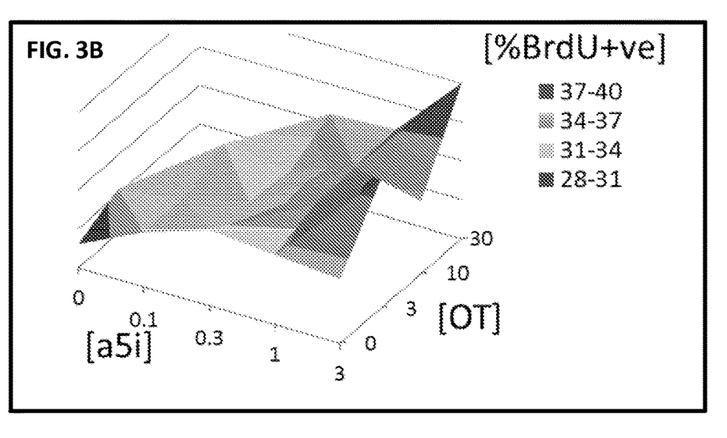
Figure 3C:
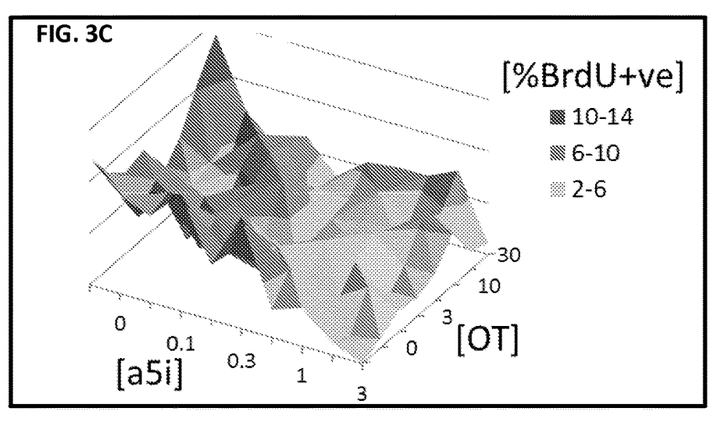

Initial doses of Alk5i+OT that enhance proliferation of primary myoblasts and neural precursor cells (NPCs) in the low mitogen media and the doses that enhance myogenic proliferation of old satellite cells in old serum (better than OT and Alk5 alone at such doses) have been defined (FIG. 3A-C).

FIGS. 3A-3C depict dose-curve matrices of OT, Alk5i and OT+Alk5i effects on myogenic and neurogenic cell proliferation. FIGS. 3A-3C show the effect of the indicated concentrations of OT (in nM) and Alk5-inhibitor (a5i, µM) on primary myoblasts in Opti-MEM (FIG. 3A); on old satellite cells isolated from 3 DPI muscle in Opti-MEM with 5% old mouse serum (FIG. 3B); and on rat neural precursor cells in basal medium (DMEM/F12/N2) (FIG. 3C). Cells were pulsed with BrdU, and BrdU immunodetection and Hoechst staining were performed. Percent proliferating cells (myogenic and neurogenic) were quantified (manually, by ImageJ and by Molecular Devices ImageXpress Micro automated epifluorescence imager, with automated cell quantification by MetaXpress). Shown is the percent proliferation visualized as a topographic map.

Alk5i has bi-phasic effect on myoblast proliferation (consistent with the bi-phasic effects of TGF-β1 that is needed at some levels, but becomes inhibitory when elevated. At certain doses OT+Alk5i enhance myoblasts, old satellite cell and NPC proliferation more than each molecule alone. Increase in Alk5i diminishes proliferation of NPCs, which have low endogenous pSmad2,3; hence TGF-β1/pSmad is needed for NPC proliferation at some levels; interestingly OT+Alk5i rescues NPC proliferation, suggesting pathway cross-talk.

Example 2: Epistasis Between TGF-Beta1 and Oxytocin

Further support for the advantages of the combined administration of OT and Alk5i comes from the observation of epistasis between the TGF-beta1 and oxytocin. While ectopic TGF-beta 1 inhibited muscle regeneration in even young muscle after an injury in mice, systemic OT rescued muscle regeneration after an injury in mice administered with ectopic TGF-beta1.

Figure 4A:
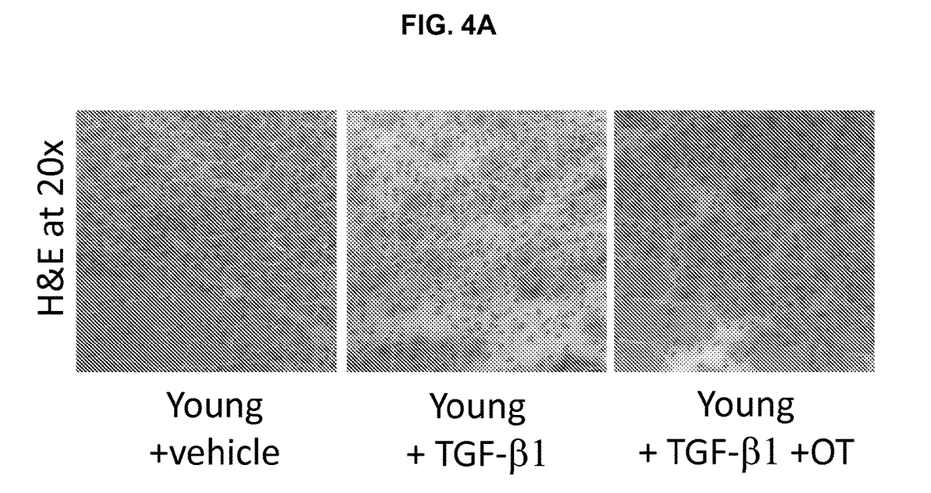
FIGS. 4A and 4B depict in vivo epistasis between TGFβ1 and Oxytocin.
Figure 4B:
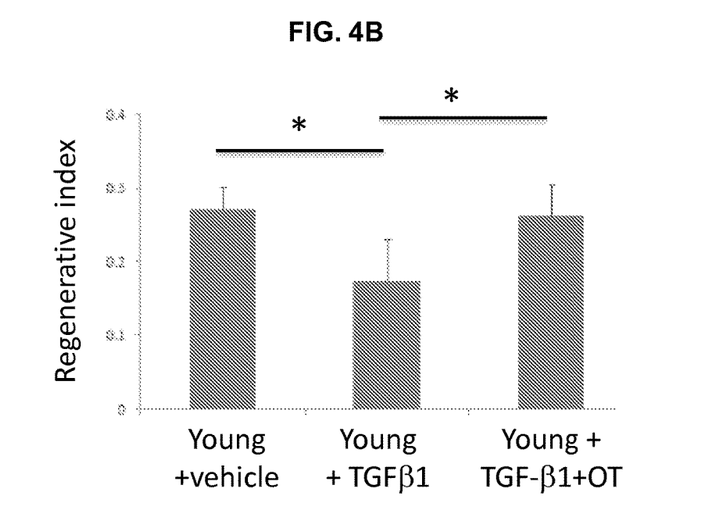

FIGS. 4A and 4B show the in vivo epistasis between TGFβ1 and Oxytocin. Young (3 mo) mouse TA muscles were injured with CTX with or without recombinant TGFβ1 (20 ng/muscle), and mice were administered 1 μg/g OT or vehicle (HBSS) by subcutaneous delivery into circulation. TGFβ1 or vehicle and OT were administered again the following day. Mice were sacrificed 5 days after injury and muscle sectioned for histological examination (with Hematoxilin and Eosin staining) in 10 um cryosections. All samples were processed and analyzed in a blinded study. FIG. 4A shows young control muscle regenerates well with many newly formed small muscle fibers with central nuclei. Ectopic TGFβ1 promotes scarring (white areas) and increased numbers of infiltrating mono-nucleated leukocytes in the young muscle, as typical of old poorly regenerating tissue. Systemic OT rescues the regeneration of young muscle injected with TGFβ1 making it similar to that of young muscle control. FIG. 4B depicts the regenerative index of the three different conditions. The regenerative index was quantified by expressing the number of newly formed fibers over total nuclei in the injury/regeneration sites; *$p<0.01$.

Example 3: Optimal Doses of Alk5i and Oxytocin that Enhance Proliferation and Attenuate CDKIs of Muscle and Neural Cells The doses of Alk5i and Oxytocin (OT) that enhance proliferation and attenuate CDKIs while minimally interfering with pSmad2, 3 and pERK will be studied in primary myoblasts and NPCs cultured in low mitogen medium.

Primary myoblasts and separately, NPCs will be plated for 24 hours at $10^3$ cells in 100 μl per well in 96 well plates in mitogen-free medium (Opti-MEM and Neurobasal A/B27, respectively) and exposed to the dose curve of concentrations of the Alk5i (Enzo ALX-270-445) and OT (Anaspec #24275). The effects of single molecules and their combinations at a wide range of doses (from 30 uM to 1 uM for OT, from 3 uM to 0.1 uM) will be tested. Myoblasts and NPCs will be pulsed with BrdU for the last 4 hours of culture and analyzed by immunofluorescence with anti-BrdU antibodies. Percent of proliferating BrdU+ cells out of total Hoechst+ cells will be quantified.

CDKIs expression and pSmad2, 3, as well as, pERK signaling intensities will be determined in these primary myoblasts and NPCs exposed to the range of Alk5i and OT concentrations by qRT PCR (for CDKIs, using specific primers and GAPDH signal for normalization) and by Western Blotting using anti-p15, p16, p21 and p27 antibodies; anti-pSmad2, anti-pSmad3 antibodies and anti-pERK1, 2 antibodies. The levels of these proteins will be normalized by the housekeeping genes (e.g. GAPDH or cytoplasmic beta-actin) and for the phosphorylated proteins also by the total Smad 2 and 3 (for pSmads) and by total ERK (for pERK1, 2). The levels of CDKIs, pSmads and pERKs will be quantified, based on the normalized pixel density. $10^4$ cells will be used for qRT PCR and $5\times10^5$ cells per Western Blotting.

The optimal doses of Alk5i and OT that enhance myogenicity of freshly isolated old muscle stem cells cultured with old mouse serum and down-regulate CDKIs in these cells, while not changing the pSmad 2, 3 and pERK significantly below/above (respectively) the young range, will be defined.

Myofiber-associated muscle stem cells will be derived from cardiotoxin-injured muscles of young and old mice and will be cultured at $10^3$ cells per well of 96 well plates, in 100 μl of Opti-MEM with 5% of their own serum (young or old) per well. These freshly isolated muscle stem cells will be exposed to the above-specified range of Alk5i and OT concentrations for 24 hours, examining the effects of single molecules and their mixture. By 24 hours in these conditions, activated by injury, young satellite cells form robustly proliferating myogenic colonies, while such proliferation of the aged myofiber-associated satellite cells is dramatically diminished. BrdU and Pax7 as well as the Ki67 and Pax7 co-detection will be used to determine the proliferation efficiency of muscle stem cells (in the presence of their own serum). Hoechst will label all nuclei. BrdU will be added for the last 4 hours of culture. The percent of BrdU+/Pax7+ and Ki67+/Pax7+ cells out of total Hoechst+ cells will be identified.

qRT PCR for CDKIs and Western Blotting for pSmad2, 3, pERK1, 2 and CDKIs p15, p16, p21 and p27 will be performed, using $5\times10^4$ cells for each qRT PCR assay and $1\times10^5$ cells per each Western Blotting; the expression levels of these proteins will be quantified, as described above for primary myoblasts.

The doses of Alk5i and OT that enhance proliferation of myoblasts and of NPCs in the low mitogen medium and the doses that enhance myogenic proliferation of old satellite cells in old serum will be identified. When added together, Alk5i and OT will have such an effect at lower doses then when used alone. Attenuation of pSmad2, 3 by Alk5i and induction of pERK1, 2 by OT will be less pronounced when these molecules are combined at low doses, while the down-regulation of CDKIs will be stronger than produced by each molecule at such low dose alone. Differences in the dose-curve effects of Alk5i, OT and Alk5i+OT between myoblasts and NPCs will be revealed. Rat and mouse NPCs respond similarly to the attenuation of TGF-beta and will internally control the results.

Materials and Methods

Animal Strains: C57.B6 male and female 2-3 month old mice (young mice) will be obtained from Jackson Labs; C57.B6 male and female 22-24 month old mice (old mice) will be obtained from the NIA. B6; 129S-Oxttm1Wsy/J male mice will be obtained from Jackson Labs, and bred, genotyped and aged. These Ot knockout mice display premature sarcopenia (smaller muscle, smaller fiber size, markedly decreased muscle regeneration after CTX injury, significantly diminished activation/proliferation of muscle stem cells, and pronounced obesity).

Isolation of Muscle Stem Cells and Primary Myoblasts: Tibialis Anterior (TA) and Gastrocneimus (Gastroc) muscles will undergo enzymatic digestion with collagenase type II. Fat pads and tendons will be removed and rounds of muscle trituration and sedimentation will purify myofibers with associated muscle stem (satellite) cells. Myofibers will be incubated with collagenase type II and dispase; suspensions will be vortexed to release satellite cells from digested fibers, passed through a cell strainer and pre-plated on uncoated dishes for 20 minutes at 37° C., 5% $CO_2$. Cells that do not adhere during pre-plating are ~95% pure (Pax7+ and/or Myf5+) robustly myogenic muscle stem (satellite) cells. Primary proliferating myoblast cell lines (Pax7+, MyoD+, desmin+) are generated from these muscle stem cells by 1-2 weeks of culture in Ham's F10, 20% FBS, 5 ng/ml FGF-2. In Opti-MEM and in DMEM, 2% horse serum, these primary myoblasts differentiate into myocytes and myotubes or become non-mitotic reserve cells.

Isolation and Culture of Neural Progenitor Cells: Primary rat neural progenitor cells (NPCs) isolated from the hippocampi of Fisher 344 rats (Charles River) will be maintained in DMEM/F12 (Life Technologies) containing N2 supplement (Life Technologies) and 10 ng/mL FGF-2 (PeproTech) on laminin (Roche) and polyornithine (Sigma) coated tissue culture plates. Primary mouse NPCs will be isolated from hippocampi of young male C57B6 mice and maintained in Neurobasal A medium (Gibco) with B27 supplement (Gibco), Glutamax-1 supplement (Gibco), 20 ng/mL FGF-2 (Peprotech), and 20 ng/mL EGF on Poly-d-Lysine and Laminin coated tissue culture plates. Primary mouse NPCs will be isolated from Ot knockout mice in a similar manner.

Statistical Analysis: Quantification and statistical Analysis by ANOVA will be performed for 3-5 entirely independent experiments, (starting with muscle stem cell preparation, myoblasts or NPCs, and all in vivo studies) and cell proliferation, qRT PCR, Qiagen and R&D arrays, Western Blotting, tissue histology and sections immunofluorescence, Echo-MRI and muscle strength assays with be performed in triplicate. These numbers are based on power analysis and IACUC considerations, and all data will be assessed for significance based on p values and heteroscedastic variance between groups that are statistically compared. Data will be analyzed using Student's t-tests (two-tailed) and P values equal or lower than 0.05 will be considered statistically significant. For quantification of immunofluorescent images for BrdU incorporation into cells, 25 20× images per replicate will be taken on the Molecular Devices ImageXpress Micro automated epifluorescence imager, followed by automated cell quantification using the multiwavelength cell-scoring module within the MetaXpress analysis software. For pixel density in Western Blotting, Gene Jockey will used to determine integrated pixel intensity with subtracted background, normalized by the pixel density of housekeeping genes and for pSmads and pERKs also by the un-phosphorylated total ERK and Smads. The data will be integrated such that for every Alk5i and OT dose (alone and as a mix) the rate of proliferation, myogenesis, neurogenesis, etc. and the levels of studied CDKIs, pSmads and pERKs are correlated. Statistics for muscle mass, degree of fibrosis, fiber size—Ferrets' diameter, the efficiency of muscle repair after CTX injury will be performed. For quantification of the number of neurogenic cells, unbiased stereology (Zeiss Axio Imager, software by MicroBrightfield) using the optical fractionator method will be performed on 8 vibratome coronal brain slices spanning the hippocampus (40 microns thick, 200 microns apart), and the number of selected cells will be normalized by the volume of hippocampal tissue. Cell numbers will be normalized to the volume of the DG granule cell layer measured by ImageJ. For pixel intensity and percent area quantifications of immunofluorescent images, MetaXpress Analysis Software will be used.

Example 4: Relationship Between TGF-Beta/pSmad2, 3 and OT/MAPK In Vivo

In the pharmacological approach, systemic Alk5i will be administered simultaneously with the antagonist of oxytocin, OTA (L-371,257 Tocris #2410) and in separate experiments, systemic OT will be delivered simultaneously with ectopic TGF-beta1 to mice. Each molecule alone (Alk5i, OT, OTA and TGF-beta1) and control vehicle (HBSS) will be used for comparison. The regeneration of TA and Gastroc muscle after an injury and ongoing neurogenesis (SGZ) will be assayed. Young (2-3 mo) C57.B6 male mice will be used in these studies, due to expected higher signal to noise ratio: old animals already have high levels of TGFβ1/pSmad2, 3 and low levels of OT/MAPK; and in old mice, Alk5i alone significantly enhances myogenesis and neurogenesis while OT alone significantly enhances muscle maintenance and repair.

Physiologically effective doses of these molecules will be used. C57b6 young male mice will have intraperitoneal delivery of TGF-β1 Type I Receptor Kinase Alk5 inhibitor, Alk5i, 2-(3-(6-Methylpyridin-2-yl)-1H-pyrazol-4-yl)-1,5-naphthyridine (Enzo ALX-270-445 0.2 nmol/g mouse in sunflower oil), alone or together with OTA (L-371,257 Tocris #2410 2 µg/g mouse); and in separate experiments, with TGF-beta1 (R&D systems), alone or together with OT (Anaspec #24275 1 ug/g mouse). Mice will receive 20 µl injections of these molecules or vehicle control (HBSS) once daily for 9-14 days (4 days prior to muscle injury and then daily for 5-10 days). TA and Gastroc muscle will be injured with cardiotoxin (CTX) and muscle will be isolated postmortem, at 3 days, 5 days and 10 days post injury (DPI). The animals will receive 7 daily IP BrdU/EDU injections: (50 mg/kg of body weight) to label mitotic cells. Four hours (or alternatively, 5 days) after receiving the last BrdU/EDU IP injection, the mice will be perfused, and brains and TAs, Gastrocs will be collected for analysis. The effects of the down-modulation of TGF-beta/pSmad3 signaling when OT is inhibited by OTA and the effects of elevated TGF-beta1 in the presence of ectopic OT will be determined by assaying muscle repair and the efficiency of hippocampal neurogenesis (as compared to: control vehicle, OTA alone and TGF-beta1 alone).

Muscle injury and the efficiency of muscle regeneration will be determined. Gastroc and TA muscles will be injected with cardiotoxin 1 (CTX, Sigma). For myogenic proliferation BrdU/EDU and desmin, as well as Ki67 and Pax7 will be co-immuno detected in 10 um muscle sections (derived from muscle isolated at 3 days post injury); for muscle repair, 10 um muscle sections (derived from muscle isolated at 5 and 10 days post injury) will be stained with Hematoxylin and Eosin and Gomori trichrome for histology analysis and assaying fibrotic index; and immunodetection of eMyHC and BrdU/EDU will be used to quantify throughout the injury site the numbers of de novo eMyHC+ myofibers with centrally-located BrdU+/EDU+ nuclei that robustly appear in young, but are lacking in the old injured muscle.

The efficiency of hippocampal neurogenesis will be determined. Mice will be anesthetized and perfused with saline and 4% PFA. Brains will be collected and placed in 4% PFA overnight, followed by dehydration in 30% sucrose/PBS at 4° C. for 2 days and sectioning at 40 μm using a vibratome. Sections will be co-immunostained with antibodies to Sox-2 and BrdU or EDU (to determine the numbers of proliferative neural stem cells). After a longer chase period (5 days after the last BrdU or EDU injections) co-immunodetection of Doublecortin (DCX) and BrdU or EDU will be used to identify the numbers of more downstream type 2b Doublecortin expressing transit amplifying cells. Immunodetection will be performed, and images will be taken with a prairie confocal microscope.

CDKIs expression and pSmad2, 3, pERK1, 2 levels in vivo will be determined at all studied time points in $5 \times 10^5$ freshly-derived muscle stem cells from TA and Gastroc and in dissected hippocampi of these mice by qRT PCR (for CDKIs) and by Western Blotting for CDKIs, pSmad2, pSmad3, pERK1, 2. Pixel intensity of pSmad2, 3, pERK1, 2 and of CDKI will be assayed in Pax7+ cells of TA and in Sox-2+ cells and Doublecortin+ cells of SGZ by immunofluorescence in tissue sections.

In the genetic approach, Alk5 inhibitor will be administered to 1-year-old Ot KO mice and effects on myogenesis and hippocampal neurogenesis will be studied. Age-matched WT littermates and young (2-3 mo) Ot KO mice will serve as controls for all experiments.

B6;129S-Oxttm1Wsy/J male mice will be purchased from Jackson Labs and bred, genotyped and aged. While there are no developmental or early life defects, by 1 year of age, as compared to the WT littermates, Ot KO mice display premature sarcopenia: smaller muscle, smaller fiber size, markedly decreased muscle regeneration after CTX injury and significantly diminished activation/proliferation of muscle stem cells, as well as pronounced obesity.

Alk5i (Enzo ALX-270-445 0.2 nmol/g mouse) will be administered intraperitoneally to the 1 year old Ot KO male mice for 9-14 days (4 days prior to muscle injury and then daily for 5-10 days). TA and Gastroc muscle will be injured with CTX, and muscle will be isolated postmortem, at 3, 5 and 10 days post injury. Prior to sacrifice, the animals will receive 7 daily IP BrdU/EDU injections: (50 mg/kg of body weight) to label mitotic cells. Four hours (or alternatively, 5 days) after receiving the last BrdU/EDU injection, the mice will be perfused, and brains and TAs, Gastrocs will be collected for analysis.

The effects of the down-modulation of TGF-beta/pSmad3 signaling when OT is genetically lacking will be determined by assaying muscle maintenance and repair and hippocampal neurogenesis. For muscle, muscle mass, fiber size, the efficiency of muscle repair after CTX injury (numbers of de-novo eMyHC+ myofibers and degree of fibrosis and the activation/proliferation of muscle stem cells in vivo), muscle strength, and body fat content (by Echo-MRI). The efficiency of hippocampal neurogenesis will be assayed by quantifying the numbers of proliferating Sox-2+ neural stem cells and Doublecortin+ cells.

CDKIs, pSmad2, 3, and MAPK/pERK levels will be determined at all studied time points in $5 \times 10^5$ freshly derived muscle stem cells (TA, Gastroc) and in dissected hippocampi of these 1 year old Ot KO mice administered with Alk5i, or vehicle control (using cells and tissues of WT littermates and of 2-3 mo Ot KO mice for comparison). Cells and tissues will be studied upon isolation by qRT PCR (for CDKIs, with specific primers, using GAPDH for normalization) and by Western Blotting on p15, p16, p21, p27, pSmad2, 3, pERK1, 2. Pixel intensity of pSmad2, 3, pERK1, 2 and of CDKI will be also assayed in Pax7+ cells of TA and in Sox-2+ cells and Doublecortin+ cells of SGZ of these Ot KO mice treated with Alk5i, or vehicle control, by immunofluorescence in tissue sections.

Whether attenuation of TGF-beta/pSmad2, 3 by Alk5i overrides the inhibitory effects of oxytocin antagonist on myogenesis and/or neurogenesis possibly down-regulating CDKIs in muscle and/or hippocampus will be determined. It will be determined that Alk5i simultaneously enhances myogenesis and neurogenesis and attenuates CDKIs in old WT mice. Whether ectopic oxytocin can ameliorate the inhibitory effects of excessive TGF-beta1 on hippocampal neurogenesis and myogenesis and reduce CDKIs will also be determined. A correlation between tissue maintenance and repair in Ot KO animals and the levels of CDKIs in their myogenic and neurogenic regions will be defined.

Example 5: Comparison of the Effects of Systemic Administration of Alk5i and OT Mixtures to Old Male and Female Mice to Heterochronic Parabiosis Heterochronic parabiosis studies have provided a proof of principle that tissue stem cells residing in an old mammal are capable of productive regenerative responses; boosting old stem cells can enhance the maintenance and repair of multiple organs, preventing or ameliorating debilitating degeneration of muscle, bone, liver, brain, etc. that invariably accompany human aging. Importantly, young mice sharing blood with old animals experienced a regenerative decline in a number of tissues demonstrating the presence of systemic inhibitors of stem cell responses in the old circulation. Studies on heterochronic parabiosis suggest that the activity of tissue stem cells can be modulated by systemic factors that change with age.

The degree to which longer-term simultaneous systemic administration of Alk5i and OT (2-3 months) emulates the positive effects of heterochronic parabiosis on myogenesis, hippocampal neurogenesis and liver regeneration in old mice, will be tested. Muscle mass and contractile strength, fiber size, lean vs. fat body content, tumor pathologies and the expression of key tumor suppressors and oncogenes will be examined. Male and female C57.B6 mice will be used.

Physiologically effective doses of these molecules that produce significant results in muscle and brain will be used: for Alk5i alone (2 ug/g mouse) and OT alone (1 ug/g mouse). Alk5i+OT will be used at the optimal doses (lower than each molecule alone) that enhance myogenic proliferation of old muscle stem cells cultured with old (e.g., 0.2 ug/g/day mouse for Alk5i and 0.1 ug/g/day mouse for OT). Subcutaneous Alzet pumps will be used for continuous delivery into circulation of these molecules or vehicle control (HBSS) for 2-3 months.

Heterochronic parabiosis will be established between young (2-3 mo) and old (22-24 mo) C57B6 mice. Male-to-male and female-to-female pairs will be used. Control isochronic parabioses will be between two animals of the same age and gender (i.e. old male pairs, old female pairs, young male pairs and young female pairs). One partner will be GFP transgenic (Jackson #006567). Blood chimerism is established by 7-10 days of parabiosis and will be tested by assaying GFP+ leukocytes in circulation of C57.B6 mice (by FACS from tail bleeds).

Assays of muscle regeneration after CTX injury will be performed by quantifying in 10 um muscle sections myogenic cell proliferation at 3 days post injury and the formation of de novo eMyHC+ myofibers, and the fibrotic index at 5 and 10 days post injury. The "Fibrotic Index" will be calculated as:

(1−(total eMyHC+fibers area/total injury area)×100%

One week prior to sacrifice the animals will receive 7 daily IP BrdU/EDU injections: (50 mg/kg of body weight). Four hours (or alternatively, 5 days) after receiving the last BrdU/EDU IP injection, the mice will be perfused, and hippocampal neurogenesis will be assayed by quantifying in brain sections the numbers of proliferating Sox-2+ cells in SGZ and of type 2b Doublecortin expressing transit amplifying cells.

Liver maintenance/ongoing hepatocyte proliferation will be assayed by quantifying albumin+Ki67+ and albumin+ BrdU+ hepatocytes near portals in 10 um tissue sections.

CDKIs expression and pSmad2, 3, pERK1, 2 levels: will be determined at all studied time points in $1\text{-}5\times10^5$ freshly-derived muscle satellite cells from TA and Gastroc and in dissected hippocampi of these mice by qRT PCR (for CDIKs) and by Western Blotting for CDKIs, apSmad2, pSmad3, pERK1, 2. Pixel intensity of pSmad2, 3, pERK1, 2 and of CDKI will be assayed in Pax7+ cells of TA and in Sox-2+ cells and Doublecortin+ cells of SGZ by immunofluorescence in tissue sections.

Muscle mass, size, fiber diameter will be determined for uninjured and CTX injured muscle (TA and Gastroc) at 10 and 14 days post injury. TA and Gastroc muscle will be weighed, fiber surface area and Feret's minimum diameter will be measured using Image J software muscle cross-sections. Volumetric measurements of intramuscular and perimuscular fat will be also performed in dissected hind legs. Lean vs. fat body content will be determined by Echo-MRI on live mice.

For direct assay of muscle strength, perimortem muscle force generation will be performed. The TA tendon will be tied with a 5-0 silk thread in order to attach the muscle to a force transducer electric stimulator (Grass Tech, Astro-Med Inc.). Supramaximal voltage square wave pulses will be performed at duration of 0.1 ms at the muscle's optimal length. Tetanic single trains will be performed at a duration of 0.5 s. Max isometric tetanic force will be determined by the frequency at which no increase in tetanic force is seen. Data will be acquired through a polyview 16 chart recorder (Grass Tech, Astro-Med Inc.) at a sampling rate of 4000 Hz. Muscle twitch force, maximum isometric contractile force, maximum rate of force development, rate of muscle relaxation will be calculated and normalized to its wet weight and cross section area.

Presence and types of cancers will be analyzed by pathology and the propensity for oncogenic transformations will be studied using manufacturers' protocols by The Mouse Oncogenes & Tumor Suppressor Genes RT² Profiler™, PyroMark CpG Assays (Qiagen), and Proteome Profiler Mouse Phospho-RTK Array Kit, (R&D) in samples of muscle, brain, liver, lung, ovaries, testes, mammary, colon, intestine, bone, etc.

The effects of Alk5i on TGF-beta/pSmad2, 3 and OT/MAPK will be compared with those of heterochronic parabiosis. Alk5i+OT mix (where each molecule is used at a lower dose than when added alone) will attenuate CDKIs without overtly altering the pSmad 2, 3 and pERK1, 2. The effects of heterochronic parabiosis on pSmad2, 3, pERK1, 3 and CDKIs will be comparatively determined in males and females. Young males and females will serve as gender-specific positive controls. Gender-specific differences will be uncovered in the old male and female mice treated with Alk5i, or OT, or Alk5i+OT.

What is claimed is:

1. A method of enhancing proliferation of a somatic cell, the method comprising:
   contacting a somatic cell with oxytocin receptor (OXTR) agonist and ALK5 antagonist,
   wherein the contacting is with an amount of the OXTR agonist and ALK5 antagonist effective to enhance proliferation of the somatic cell.

2. The method of claim 1, wherein the somatic cell is a muscle cell.

3. The method of claim 2, wherein the muscle cell is a skeletal muscle cell.

4. The method of claim 3, wherein the skeletal muscle cell is a myoblast.

5. The method of claim 1, wherein the somatic cell is an activated satellite cell.

6. The method of claim 1, wherein the somatic cell is a neural cell.

7. The method of claim 6, wherein the neural cell is a neural stem cell.

8. The method of claim 6, wherein the neural cell is a neural progenitor cells.

9. The method of claim 1, wherein the somatic cell is an adult human stem or an adult human progenitor cell.

10. The method of claim 1, wherein the somatic cell is cell of an aged subject.

11. The method of claim 1, wherein the somatic cell is an injured cell.

12. The method of claim 11, wherein the injury is caused by a disease.

13. The method of claim 1, wherein the somatic cell is a diseased cell.

14. The method of claim 1, wherein the amount of the OXTR agonist is in the range of 7.5 nM-30 nM.

15. The method of claim 1, wherein the amount of the ALK5 antagonist is in the range of 0.05 μM-3 μM.

16. The method of claim 1, wherein the ratio of the OXTR agonist to the ALK5 antagonist is 1:50.

17. The method of claim 1, wherein the ratio of the OXTR agonist to the ALK5 antagonist is 50:1.

18. The method of claim 1, wherein the ratio of the OXTR agonist to the ALK5 antagonist is 1:40.

19. The method of claim 1, wherein the ratio of the OXTR agonist to the ALK5 antagonist is 1:40.

20. The method of claim 1, wherein the ratio of the OXTR agonist to the ALK5 antagonist is 40:1.

21. The method of claim 1, wherein the ratio of the OXTR agonist to the ALK5 antagonist is 1:25.

22. The method of claim 1, wherein the ratio of the OXTR agonist to the ALK5 antagonist is 25:1.

23. The method of claim 1, wherein the ratio of the OXTR agonist to the ALK5 antagonist is 1:10.

24. The method of claim 1, wherein the ratio of the OXTR agonist to the ALK5 antagonist is 10:1.

25. The method of claim 1, wherein the ratio of the OXTR agonist to the ALK5 antagonist is 1:5.

26. The method of claim 1, wherein the ratio of the OXTR agonist to the ALK5 antagonist is 5:1.

27. The method of claim 1, wherein the ratio of the OXTR agonist to the ALK5 antagonist is 1:1.

28. The method of claim 1, wherein the OXTR agonist is oxytocin.

29. The method of claim 1, wherein the ALK5 antagonist is 2-(3-(6-Methylpyridin-2-yl)-1H-pyrazol-4-yl)-1,5-naphthyridine.

30. The method of claim 1, wherein the proliferation of the somatic cell is reduced as compared to the proliferation of the same type of somatic cell from a young subject.

31. The method of claim 1, wherein the proliferation of the somatic cell is reduced as compared to the proliferation of the same type of somatic cell from a healthy adult subject.

32. The method of claim 1, further comprising assessing proliferation of the somatic cell following the contacting and adjusting the amount of the OXTR agonist and/or the ALK5 antagonist.

33. The method of claim 1, further comprising assessing proliferation of the somatic cell following the contacting and increasing the amount of the OXTR agonist.

34. The method of claim 1, further comprising assessing proliferation of the somatic cell following the contacting and decreasing the amount of the OXTR agonist.

35. The method of claim 1, further comprising assessing proliferation of the somatic cell following the contacting and increasing the amount of the ALK5 antagonist.

36. The method of claim 1, further comprising assessing proliferation of the somatic cell following the contacting and decreasing the amount of the ALK5 antagonist.

37. The method of claim 1, further comprising assessing proliferation of the somatic cell following the contacting and repeating the contacting on a schedule.

38. The method of claim 37, further comprising assessing proliferation of the somatic cell following the repeated contacting and adjusting the contacting schedule.

* * * * *